(12) United States Patent
Epstein

(10) Patent No.: US 7,744,523 B2
(45) Date of Patent: Jun. 29, 2010

(54) DRIVE CIRCUIT FOR MAGNETIC STIMULATION

(75) Inventor: Charles M. Epstein, Atlanta, GA (US)

(73) Assignee: Emory University, Atlanta, GA (US)

( * ) Notice: Subject to any disclaimer, the term of this patent is extended or adjusted under 35 U.S.C. 154(b) by 391 days.

(21) Appl. No.: 11/759,537

(22) Filed: Jun. 7, 2007

(65) Prior Publication Data

US 2008/0306326 A1 Dec. 11, 2008

(51) Int. Cl.
*A61N 2/00* (2006.01)
(52) U.S. Cl. .......................................... 600/9
(58) Field of Classification Search .............. 600/9–15
See application file for complete search history.

(56) References Cited

U.S. PATENT DOCUMENTS

| | | | |
|---|---|---|---|
| 4,712,558 A | 12/1987 | Kidd et al. | |
| 4,940,453 A | 7/1990 | Cadwell | |
| 5,047,005 A | 9/1991 | Cadwell | |
| 5,061,234 A | 10/1991 | Chaney | |
| 5,116,304 A | 5/1992 | Cadwell | |
| 5,766,124 A | 6/1998 | Polson | |
| 6,066,084 A | 5/2000 | Edrich et al. | |
| 6,123,658 A * | 9/2000 | Schweighofer et al. | 600/13 |
| 6,179,769 B1 | 1/2001 | Ishikawa et al. | |
| 6,179,770 B1 | 1/2001 | Mould | |
| 6,366,814 B1 | 4/2002 | Boveja et al. | |
| 6,463,328 B1 | 10/2002 | John | |
| 6,537,197 B1 | 3/2003 | Ruohonen et al. | |
| 6,551,233 B2 | 4/2003 | Perreault et al. | |
| 6,591,138 B1 | 7/2003 | Fischell et al. | |
| 6,663,556 B2 | 12/2003 | Barker | |
| 2001/0031906 A1 | 10/2001 | Ishikawa et al. | |
| 2002/0087201 A1 | 7/2002 | Firlik et al. | |
| 2002/0091419 A1 | 7/2002 | Firlik et al. | |
| 2002/0103515 A1 | 8/2002 | Davey et al. | |
| 2003/0088274 A1 | 5/2003 | Gliner et al. | |
| 2003/0097161 A1 | 5/2003 | Firlik et al. | |
| 2003/0125786 A1 | 7/2003 | Gliner et al. | |
| 2003/0130706 A1 | 7/2003 | Sheffield et al. | |
| 2004/0077921 A1 | 4/2004 | Becker et al. | |
| 2005/0228209 A1 | 10/2005 | Schneider et al. | |
| 2005/0261542 A1 * | 11/2005 | Riehl | 600/14 |

FOREIGN PATENT DOCUMENTS

| | | |
|---|---|---|
| WO | WO 02/32504 A2 | 4/2002 |
| WO | WO 02/072194 A2 | 9/2002 |
| WO | WO 02/085449 A2 | 10/2002 |
| WO | WO 02/085454 A1 | 10/2002 |
| WO | WO 02/094997 A2 | 11/2002 |
| WO | WO 2005/000401 A1 | 1/2005 |

* cited by examiner

*Primary Examiner*—Samuel G Gilbert
(74) *Attorney, Agent, or Firm*—Woodcock Washburn LLP

(57) ABSTRACT

The inventive technique includes devices and methods for generating a magnetic field. One such device may include an inductor for generating a magnetic field and a power source for providing power. Such a device may also include a semiconductor switching device that operatively couples the inductor and power source, wherein the semiconductor switching device directs power from the power source to the inductor to generate the magnetic field.

44 Claims, 4 Drawing Sheets

DRIVE CIRCUIT FOR MAGNETIC STIMULATION

BACKGROUND

A number of medical ailments are treated and/or diagnosed through the application of a magnetic field to an afflicted portion of a patient's body. Neurons and muscle cells are a form of biological circuitry that carry electrical signals and respond to electromagnetic stimuli. When an ordinary conductive wire loop is passed through a magnetic field or is in the presence of a changing magnetic field, an electric current is induced in the wire.

The same principle holds true for conductive biological tissue. When a changing magnetic field is applied to a portion of the body, neurons may be depolarized and stimulated. Muscles associated with the stimulated neurons can contract as though the neurons were firing by normal causes.

A nerve cell or neuron can be stimulated in a number of ways, including indirectly via transcranial magnetic stimulation (TMS), for example. TMS uses a rapidly changing magnetic field to induce a current in a nerve cell, without having to cut or penetrate the skin. The nerve is said to "fire" when a membrane potential within the nerve rises with respect to its normal negative ambient level of approximately −90 mV, depending on the type of nerve and local ionic conditions of the surrounding tissue.

The use of magnetic stimulation is very effective in rehabilitating injured or paralyzed muscle groups and may prove useful in other therapies involving peripheral nerve stimulation including, but not limited to, pain mitigation, stimulation of neovascularization, wound healing and bone growth.

Magnetic stimulation also has proven effective in stimulating regions of the brain, which is composed predominantly of neurological tissue. One area of particular interest is the treatment of depression. It is believed that more than 28 million people in the United States alone suffer from some type of neuropsychiatric disorder. These include conditions such as depression, schizophrenia, mania, obsessive-compulsive disorder, panic disorders, and others. Depression is the "common cold" of psychiatric disorders, believed to affect 19 million people in the United States and possibly 340 million people worldwide.

Modern medicine offers depression patients a number of treatment options, including several classes of anti-depressant medications (e.g., SSRI's, MAOI's and tricyclics), lithium, and electroconvulsive therapy (ECT). Yet many patients remain without satisfactory relief from the symptoms of depression. To date, ECT remains an effective therapy for resistant depression; however, many patients will not undergo the procedure because of its severe side effects.

Recently, repetitive transcranial magnetic stimulation (rTMS) has been shown to have significant anti-depressant effects for patients that do not respond to the traditional methods. The principle behind rTMS is to apply a subconvulsive stimulation to the prefrontal cortex in a repetitive manner, causing a depolarization of cortical neuron membranes. The membranes are depolarized by the induction of small electric fields in excess of 1 V/cm that are the result of a rapidly changing magnetic field applied non-invasively.

To generate a magnetic pulse that is capable of providing a therapeutic effect on a patient, TMS, rTMS and Magnetic Seizure Therapy (MST) treatments all require a great deal of electrical power, typically in the range of several hundred joules (J) per pulse. Various attempts to optimize the design of the coil used in such treatments have not been able to substantially mitigate the need for a great deal of electrical power. For example, to cause a stimulation coil to generate trains of rapid rTMS pulses, thousands of watts (W) of power are typically delivered to the coil. This amount of power leads to rapid coil heating. The amount of coil heating is so great that the coil often is heated to the point at which it would be uncomfortable or unsafe to use the coil on a patient. Thus, attempts have been made to cool stimulation coils using water, air or oil. Unfortunately, these cooling mechanisms are cumbersome, add complexity to the magnetic stimulation system, are expensive and are sometimes adversely affect the performance of the stimulator. A more advantageous approach would be to reduce the amount of power required by the magnetic stimulation device to generate a therapeutically-equivalent magnetic pulse.

SUMMARY

In view of the foregoing drawbacks and shortcomings, devices and methods for generating a magnetic field are provided. One such magnetic stimulation device may include an inductor for generating a magnetic field and a power source for providing power. Such a device may also include a semiconductor switching device that operatively couples the inductor and power source, wherein the semiconductor switching device directs power from the power source to the inductor to generate the magnetic field.

One such method may include providing power using a power source and operatively coupling the power source to an inductor using a semiconductor switching device. The method may also include directing power from the power source to the inductor using the semiconductor switching device and generating the magnetic field using the inductor.

DETAILED DESCRIPTION

Figure 1:
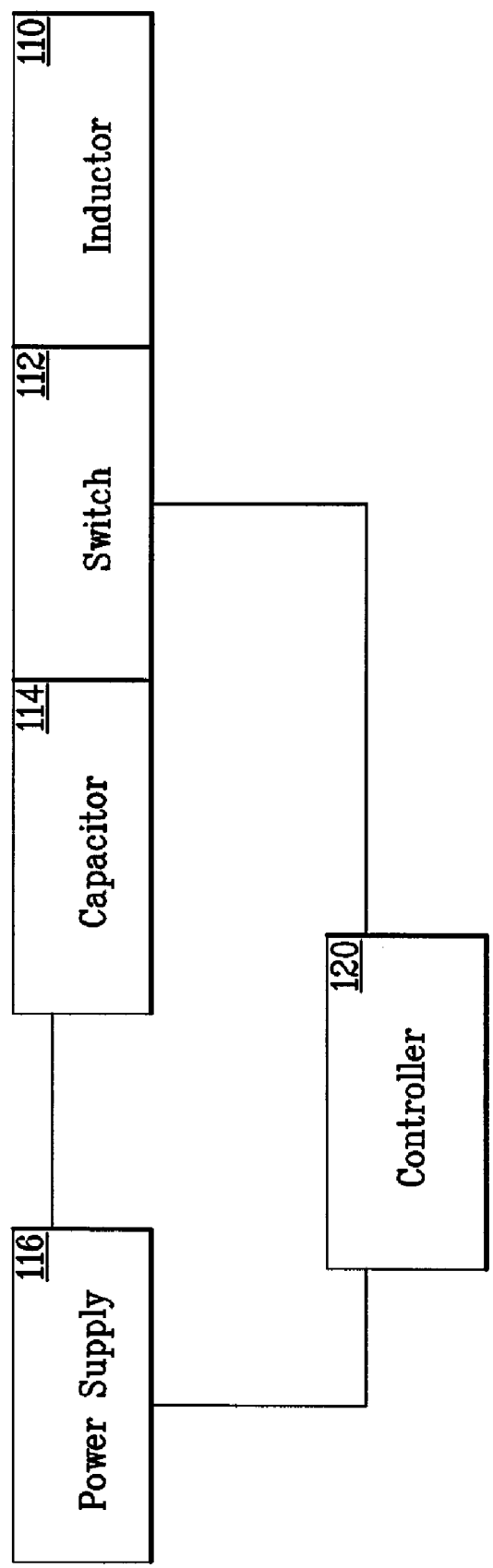
FIG. 1 is a diagram illustrating an example magnetic device according to an embodiment.

The subject matter of the disclosed embodiments is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Overview

According to an embodiment, an improved drive circuit is provided. The drive circuit may reduce the power required by a stimulation coil to generate a therapeutic magnetic pulse. As a result of the reduced power, the size and amount of heat generated by a magnetic stimulation coil may be reduced, which in turn reduces cooling requirements associated with the stimulation coil. Because of these reductions, the entire magnetic stimulation device may be made less complex, smaller and less expensive. As will be discussed below, embodiments may reduce the power requirement of TMS and rTMS by approximately 50%, which may produce a gain in efficiency of approximately 800% as compared to conventional drive circuits and stimulation coils.

Magnetic Device Overview

For purposes of explanation and context, an overview of the operation and applications of a magnetic device in which aspects of the various embodiments may be implemented is now discussed. As is well known to those skilled in the art, the magnitude of an electric field induced on a conductor is proportional to the rate of change of magnetic flux density across the conductor. When an electric field is induced in a conductor, the electric field creates a corresponding current flow in the conductor. The current flow is in the same direction of the electric field vector at a given point. The peak electric field occurs when the time rate of change of the magnetic flux density is the greatest and diminishes at other times. During a magnetic pulse, the current flows in a direction that tends to preserve the magnetic field (i.e., Lenz's Law).

As may be appreciated, various devices may take advantage of the above principles to induce an electric field, and such devices may be used in a variety of applications. For example, magnetic devices may be used for electrical stimulation of the anatomy, and the like. While the discussion herein focuses on magnetic devices that are used in connection with magnetic stimulation of anatomical tissue, it will be appreciated that such discussion is so limited solely for purposes of explanation and clarity. Thus, it will be understood that an embodiment is equally applicable to any application of a magnetic device in any field of endeavor. Thus, the present discussion of magnetic devices should not be construed as limiting embodiments of the invention to medical or other applications.

Therefore, and turning now to the context of electrical stimulation of the anatomy, certain parts of the anatomy (e.g., nerves, tissue, muscle, brain) act as a conductor and carry electric current when an electric field is applied. The electric field may be applied to these parts of the anatomy transcutaneously by applying a time varying (e.g., pulsed) magnetic field to the portion of the body. For example, in the context of TMS, a time-varying magnetic field may be applied across the skull to create an electric field in the brain tissue, which produces a current. If the induced current is of sufficient density, neuron action potential may be reduced to the extent that the membrane sodium channels open and an action potential response is created. An impulse of current is then propagated along the axon membrane that transmits information to other neurons via modulation of neurotransmitters. Such magnetic stimulation has been shown to acutely affect glucose metabolism and local blood flow in cortical tissue. In the case of major depressive disorder, neurotransmitter dysregulation and abnormal glucose metabolism in the prefrontal cortex and the connected limbic structures may be a likely pathophysiology. Repeated application of magnetic stimulation to the prefrontal cortex may produce chronic changes in neurotransmitter concentrations and metabolism so that the symptoms of depression are reduced or alleviated. While the discussion herein focuses on transcutaneous stimulation, it should be appreciated by one skilled in the art that the techniques and devices discussed herein may, in some embodiments, be applied to stimulation involving a coil that may be placed anywhere relative to a patient. In one such embodiment, for example, the coil may be placed inside or proximate to any portion of a patient's anatomy.

In a similar fashion, non-cortical neurons (e.g., cranial nerves, peripheral nerves, sensory nerves) may also be stimulated by an induced electric field. Techniques have been developed to intentionally stimulate peripheral nerves to diagnose neuropathologies by observing response times and conduction velocities in response to a pulsed magnetic field induced stimulus.

As noted above, it should be appreciated that transcutaneous magnetic stimulation is not limited to treatment of depression. In addition to depression, the transcutaneous magnetic stimulation methods and apparatus of the invention may be used to treat a patient such as a human suffering from epilepsy, schizophrenia, Parkinson's disease, Tourette's syndrome, amyotrophic lateral sclerosis (ALS), multiple sclerosis (MS), Alzheimer's disease, attention deficit/hyperactivity disorder, obesity, bipolar disorder/mania, anxiety disorders (e.g., panic disorder with and without agoraphobia, social phobia also known as social anxiety disorder, acute stress disorder and generalized anxiety disorder), post-traumatic stress disorder (one of the anxiety disorders in DSM), obsessive compulsive disorder (also one of the anxiety disorders in DSM), pain (such as, for example, migraine and trigeminal neuralgia, as well as chronic pain disorders, including neuropathic pain, e.g., pain due to diabetic neuropathy, post-herpetic neuralgia, and idiopathic pain disorders, e.g., fibromyalgia, regional myofascial pain syndromes), rehabilitation following stroke (neuro plasticity induction), tinnitus, stimulation of implanted neurons to facilitate integration, substance-related disorders (e.g., dependence, abuse and withdrawal diagnoses for alcohol, cocaine, amphetamine, caffeine, nicotine, cannabis and the like), spinal cord injury and regeneration/rehabilitation, stroke, head injury, sleep deprivation reversal, primary sleep disorders (primary insomnia, primary hypersomnia, circadian rhythm sleep disorder), cognitive enhancements, dementias, premenstrual dysphoric disorder (PMS), drug delivery systems (changing the cell membrane permeability to a drug), induction of protein synthesis (induction of transcription and translation), stuttering, aphasia, dysphagia, essential tremor, and/or eating disorders (such as bulimia, anorexia and binge eating).

Example Magnetic Stimulation Device

A ferromagnetic core may be used in connection with a magnetic device to produce a magnetic field. In some embodiments, such a magnetic field may be for purposes of carrying out transcutaneous magnetic stimulation such as, for example, Transcranial Magnetic Stimulation (TMS), Repetitive TMS (rTMS), Magnetic Seizure Therapy (MST), diagnosis of nerve conduction disorders, reduction of peripheral nerve discomfort and so forth. Again, although some of the examples that follow may be discussed in connection with TMS and rTMS embodiments for the purposes of explanation and clarity, any type of transcutaneous magnetic stimulation, including all of those listed above, may be performed according to an embodiment of the invention. In addition, and as noted above, embodiments are not limited to transcutaneous magnetic stimulation, as an embodiment may be used in connection with magnetic devices that generate a magnetic field for any purpose.

Furthermore, the embodiments presented herein are not limited to the use of ferromagnetic core magnetic stimulation devices, as other core materials may be used such as, for example, air. Such air core configurations may include, but are not limited to, windings in a "figure eight," circular, conical or double conical shape, or the like. The discussion herein therefore describes a ferromagnetic core magnetic stimulation device solely for purposes of explanation and clarity. In an embodiment, a ferromagnetic core may be substantially "C" shaped, and in another embodiment the ferromagnetic core may include a highly saturable magnetic material having a magnetic saturation of at least 0.5 Tesla. In some embodiments, a ferromagnetic core may be shaped to optimize the magnetic field distribution in the treatment area. Treatment areas for other forms of treatment (e.g., reduction of discomfort in peripheral nerves, etc.) may be more or less deep than is the case for TMS.

FIG. 1 is a diagram illustrating an example magnetic device 100. In magnetic device 100, power supply 116, capacitor 114, switch 112 and controller 120 form an electric circuit that provides a power signal to inductor 110. The power signal may be any time-varying electric signal capable of generating an electric and/or magnetic field. The inductor 110 may be used to conduct TMS, rTMS and/or Magnetic Seizure Therapy (MST), for example.

Power supply 116 may be any type of power source that provides sufficient energy for inductor 110 to generate a magnetic field for its intended purpose—whether for TMS, rTMS, MST or any other type of application. For example, power supply 116 may be a conventional 120 or 240 VAC main power source. Inductor may be any type of induction device such as, for example, a treatment coil having an air or ferromagnetic core, as was discussed above. In an embodiment, such a treatment coil may be fabricated from high saturation core materials. The treatment coil may also employ a thin core design to optimize the coil for TMS, for example. In an embodiment, a treatment coil that employs a thin core design may be constructed as a substantially C-shaped core that has been reduced in thickness, thus providing a smaller cross-sectional area, less saturable material and therefore lowered power requirements, as well as less weight, while still having a field strength that penetrates to the same depth as a conventional core design. It will be appreciated that a treatment core that employs such a thin core design may generate a magnetic field that stimulates a reduced volume of tissue in the patient.

Capacitor 114 provides energy storage for pulsing inductor 110. While capacitor 114 is described herein, it should be appreciated that capacitor 114 may, in one embodiment, be any type of energy storage device. Thus, the term "capacitor" is used herein merely as a shorthand reference to any type of energy storage device, which in one embodiment may be a capacitor. For example, in another embodiment power supply 116 may itself serve the energy storage functions of capacitor 114, thereby obviating the need for capacitor 114 itself. Capacitor 114 may be used, for example, in applications where a 120 VAC power source or the like is available. A typical doctor's office may only be equipped with a conventional (e.g., 120 VAC or the like) power supply rather than a higher-power 240 VAC or three-phase power supply. As a result, the use of capacitor 114 to store energy for use in pulsing inductor 110 may enable device 100 to operate using higher power levels than might otherwise be possible if simply using power supply 116 alone.

Power supply 116 also may be comprised of any number and type of power supplies. For example, power supply 116 may be the output of a power supply that runs off of 120 VAC and then converts the AC input power signal to a DC output power signal. Alternatively, power supply 116 may be a battery, which may be useful in applications where magnetic stimulation device is to be portable. In yet another embodiment, power supply 116 may be a combination of a power supply and a battery. It will be appreciated that such a configuration may be useful when the power required to generate a pulse, or train of pulses, exceeds the capacity (or a significant percentage of the capacity) of the power supply alone. Thus, the combined power of the power supply and battery may be used to generate the pulse(s), with the battery helping to sustain voltage during period(s) of high demand associated with the generation of the pulse(s), and then the power supply can recharge the battery in between pulses, for example. A device that incorporates such a configuration could therefore use, for example, a standard 120 VAC outlet to generate pulses that otherwise need more power than a 120 VAC outlet could provide, and/or could provide adequate power line regulation. Such a device could therefore be used in a location that has standard 120 VAC outlets such as, for example, a medical professional's office.

Capacitor 114 may include any number and/or type of capacitor(s) (or other type of energy storage devices) that are appropriate for the power level, charging time and/or pulse type required by device 100. Switch 112 may be any type of electrical switching device that can operate inductor 110 by switching power from capacitor 114 and/or power supply 116 on and off. For example, switch 112 may be operated to switch power from power supply 116 to charge capacitor 114. Switch may also be used to discharge capacitor 114 through inductor 110, thereby creating a magnetic field that can be used for TMS treatment, for example. TMS controller 120 may be any type of hardware, software, or combination thereof, that controls switch 112 and/or power supply 116.

Figure 2:
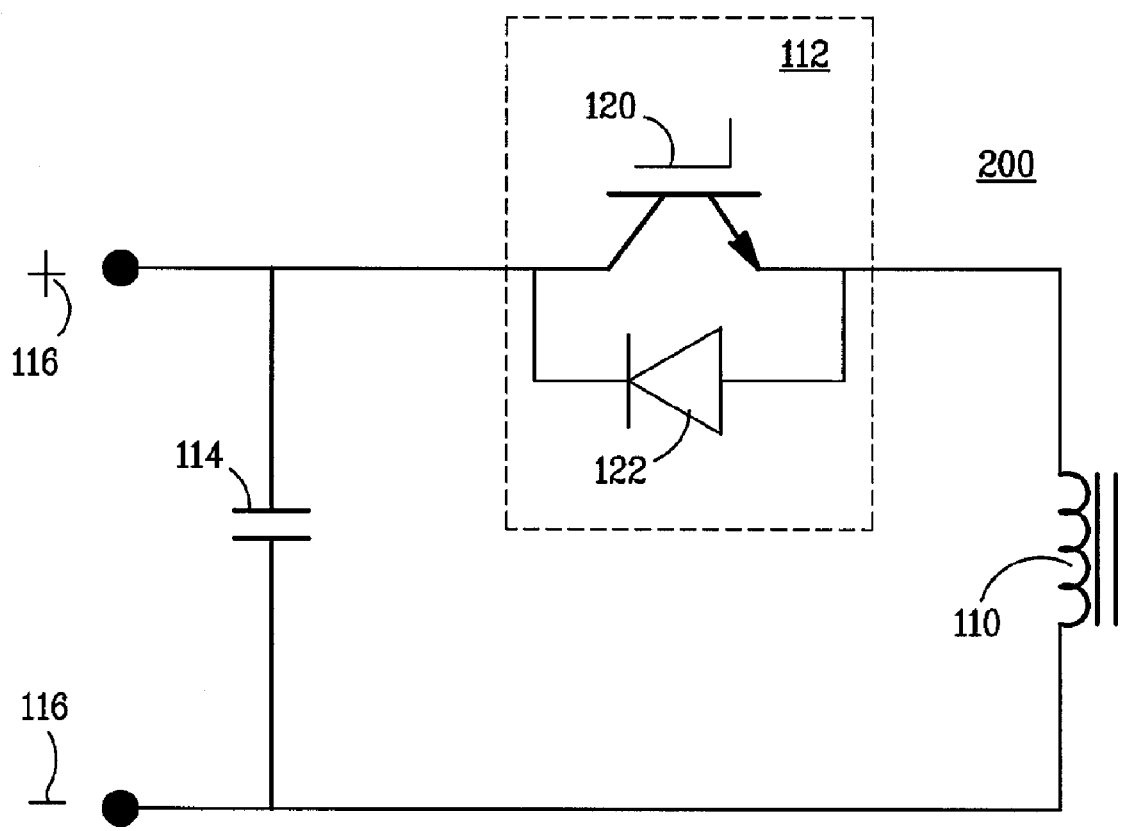
FIG. 2 is a circuit diagram illustrating an example magnetic device drive circuit according to an embodiment.

FIG. 2 is a circuit diagram illustrating an example magnetic device drive circuit 200 according to an embodiment. It will be appreciated that circuit 200 is a simplified representation of various components illustrated in FIG. 1, and that any number and type of components in addition to the components illustrated in FIGS. 1 and 2 may be used in connection with an embodiment.

It can be seen that in an embodiment circuit 200 may be comprised of power supply 116, capacitor 114, inductor 110 (which may be a stimulation coil), and switch 112, which may be formed by IGBT 120 and commutating diode 122, which may be connected in parallel. IGBT 120 may be used in an embodiment to discharge capacitor 114 into inductor 110 to generate a magnetic field. In addition, IGBT 120 may be protected from high voltage spikes by a commutating diode 122, which suppresses voltage transients. In such an embodiment, commutating diode 122 may be what is commonly referred to as a "snubber." While referred to herein as IGBT 120 for purposes of clarity, switch 112 may comprise any type of device in which a commutating circuit is employed.

It will be appreciated that while the discussion herein focuses on an embodiment in which IGBT 120 is employed, other semiconductor switching devices may be employed in connection with an embodiment. For example, in one such embodiment, an embodiment, an Integrated Gate Commutated Thyristor (IGCT) may take the place of IGBT 120 and commutating diode 122 in drive circuit 200. Other semiconductor switching devices with similar power handling and switching characteristics may be used in connection with an embodiment.

Power supply 116 may be any type of electrical power source that is appropriate for the intended function of circuit 200, or of a device in which circuit 200 is a part. For example, power supply 116 may comprise a DC power signal that has been converted (i.e., rectified) from an AC input power signal, for example. Power supply 116 may also comprise a battery or other power source, as was discussed above in FIG. 1.

As was the case above in FIG. 1, capacitor 114 may be any type of energy storage device that is capable of pulsing inductor 110 to generate a magnetic field. Inductor 110 may be a ferromagnetic (e.g, iron) or air core magnetic coil. In one embodiment, inductor 110 may be an iron core magnetic coil. It will be appreciated that a magnetic coil that employs an iron core may be able to be switched faster than a magnetic coil having an air core. In some embodiments, therefore, an iron core may be selected in applications involving the generation of short pulse widths that may be used in connection with the stimulation of cortical neurons, as will be discussed below. Regardless of the type of coil used in inductor 110, in an embodiment the shape of the coil's core and/or the number and configuration of windings may be selected to cause inductor 110 to generate a magnetic field having a desired waveform. In an embodiment, the waveform may be selected to have a desired effect on a patient, for example. For an embodiment with high voltage, high inductance, and low capacitance, the resonant frequency specified in Equation 1, below, may be much greater than would be possible with a thyristor switch, allowing more selective stimulation and greater energy efficiency.

Thus, it should be appreciated that an embodiment's combination of an iron core and a higher speed semiconductor device such as IGBT 120, IGCT or the like, may enable an increased resonance frequency (i.e., shorter pulse length), which in turn may provide for higher stimulation frequencies and more efficient stimulation of cortical neurons or axons.

In contrast to conventional magnetic stimulation devices that use a thyristor (i.e., a silicon-controlled rectifier) as a main switching element for high currents at high voltage, an embodiment employs IGBT 120 as the main switching element in place of, or in addition to, a thyristor. Thyristors have a significant turn-off time, which increases with the rated voltage and inhibits simultaneous optimization of operating frequency and operating voltage. In contrast, an embodiment provides a capacitor 114—inductor 110 resonant drive circuit 200 that uses IGBT 120 as a switching element (i.e., switch 112), and is controlled by an isolated DC pulse (provided by, for example, power source 116) and timed to turn off during the reverse phase of the stimulation pulse. IGBT 120 is capable of switching at higher frequencies than a thyristor, thereby enabling inductor 110 to generate a greater frequency range of magnetic pulses as compared to a thyristor-controlled, conventional magnetic stimulation device. As a result, a magnetic stimulation device that is switched by IGBT 120, according to an embodiment, is able to operate using lower input power than a conventional magnetic stimulation device. Such power savings may come from, for example, two sources: (1) operation at higher voltage and lower current reduces resistive losses in the circuit, leading to greater charge recovery from each pulse and also a higher second phase of the cosine pulse waveform, (where, for example, the second phase performs the work), and (2) the shorter pulse waveform is more efficient, because neuronal cell membranes are "leaky," and part of the charge transferred across the cell membrane at the beginning of the pulse is lost by the time the pulse has ended. Shorter pulses may result in less membrane loss.

A magnetic stimulation device according to an embodiment may generate, for example, rapid TMS pulses having a pulse width less than approximately 200 µs in duration (when such an embodiment is intended to stimulate cortical neurons, for example). In one embodiment, the TMS pulses may have a pulse width of approximately 100 µs-150 µs in duration. It will be appreciated that such pulse widths may be optimized for the intended target such as, for example, cortical neuron stimulation. Some IGBTs may not be able to handle high current loads. Thus, a configuration of circuit 200 may enable the use of IGBT 120 as switch 112 by lowering the amount of current while simultaneously producing an equivalent magnetic field using inductor 110. To generate a magnetic field for TMS, rTMS, MST or other stimulation applications at a given frequency in some embodiments, a balance may be struck between the inductance and capacitance values used in the drive circuit. The relationship between capacitance and inductance and their effect on a resonant circuit's frequency is governed by the well-known equation:

$$f = \frac{1}{2\pi\sqrt{LC}} \quad (1)$$

Where f is the resonant frequency, L is the inductance and C is the capacitance of the circuit. Some embodiments may achieve this balance by running inductor 110 with as low an inductance as possible (e.g., commonly on the order of 10-24 µH in a typical TMS application). As a result, the capacitance (and therefore the current used in the circuit) may need to be very large (e.g., at least 50 µF) in order for the circuit to generate the desired magnetic field. When such a circuit is designed to run in this manner, parasitic energy losses and stray inductances may require additional components (such as cooling equipment) to compensate for the problem. In addition, the use of IGBT 120 as switch 112 may be precluded in such a configuration because of the high current levels that are present.

An embodiment may use high inductance (on the order of approximately 50-55 µH in the typical TMS application referred to above, for example) in inductor 110. In addition, the capacitance of capacitor 114 may be reduced to a value of approximately 7 µF. The current in circuit 200 is therefore reduced, and the voltage is increased. For example, a device according to an embodiment may operate at approximately 1,200 A. Likewise, such a device may operate at approximately 3,000 V, for example.

It may be appreciated that such increased voltage may result in some additional voltage-dependent losses, but the types of losses that occur from high voltage are typically easier to account for than losses that occur from high current. Thus, additional efficiencies may be achieved by an embodiment.

According to such an embodiment, such a drive circuit 100 may be capable of operating at approximately twice the frequency and approximately ½ to ⅛ the peak current of conventional systems. This very low current requirement may lead to lower resistive loss in inductor 130, even at the uniquely high inductance of 50-55 µH, for example. The result is reduced inductor 130 heating and bulk, higher charge recovery. In a TMS, rTMS or MST system, such improvements may result in more efficient brain stimulation with a net reduction in power consumption of approximately 50% beyond that attained with conventional systems. In an alternative embodiment, circuit 100 also may be implemented with an integrated gate commutated thyristor (IGCT) or other modern switching element in place of or in addition to IGBT 120. It will be appreciated that the exact values for inductor 110, capacitor 114, etc., may be determined based on the intended application (e.g., TMS, rTMS, MST and the like).

Figure 3:
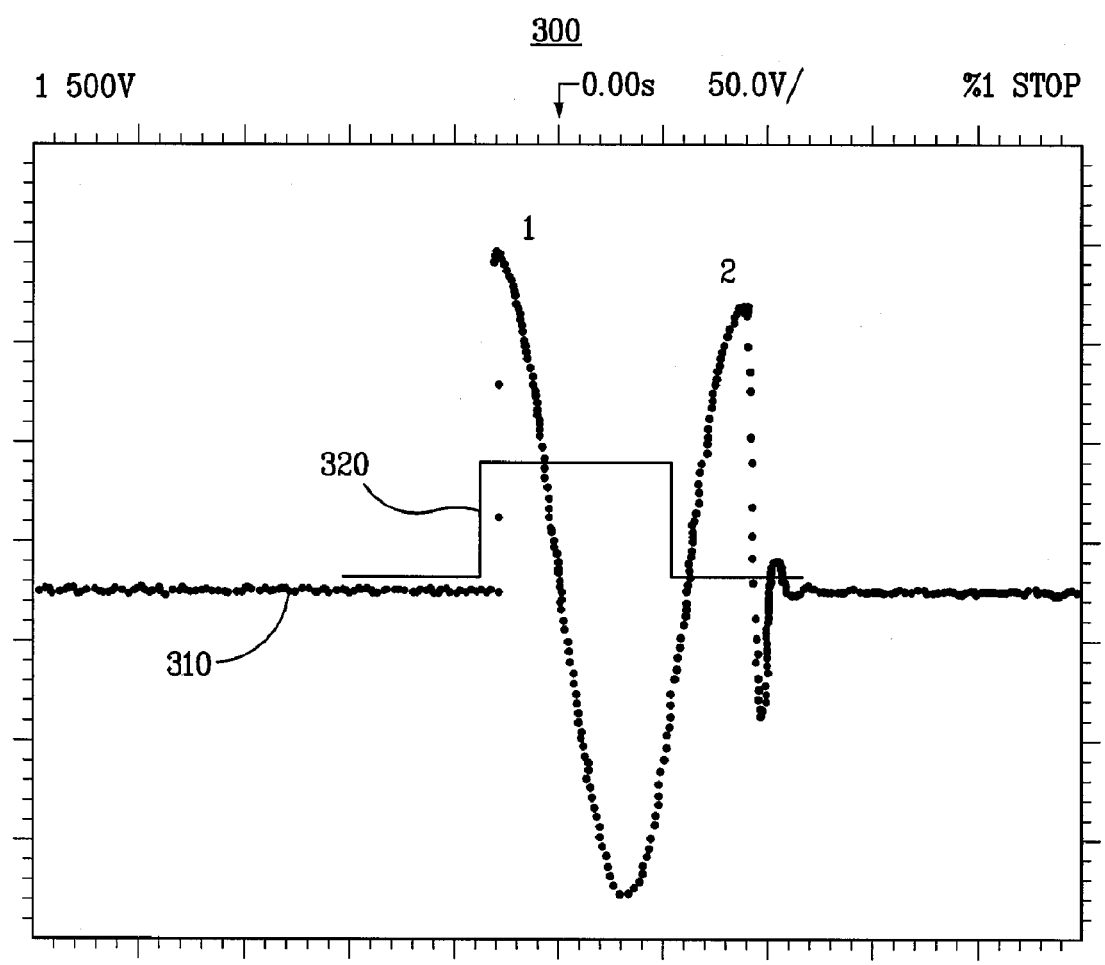
FIG. 3 is a screen shot illustrating an example plot of voltage across an inductor in accordance with an embodiment.

To further explain the benefits that result from the use of IGBT 120 as a switching element, reference is now made to FIG. 3. FIG. 3 is a screen shot 300 illustrating an example plot 310 of voltage across an inductor (such as inductor 110 discussed above in connection with FIGS. 1 and 2) in accordance with an embodiment during one TMS pulse. Line 320 shows the timing of the IGBT trigger pulse (which may not be to the same voltage scale as plot 310). The difference between the amplitudes of peak 1 and peak 2 represents resistive loss in the inductor and in other circuitry. The trigger pulse, which controls the IGBT switch, ends at a time when current is being conducted through the back diode 122 in FIG. 2, and not through the IGBT proper. This timing prevents inadvertent destruction of the IGBT or other circuit elements. Compared with peak 1 in the voltage plot, peak 2 is relatively higher than in typical thyristor-gated drive circuits because of operation at higher voltage and lower current, with lower resistive loss as described above.

Figure 4:
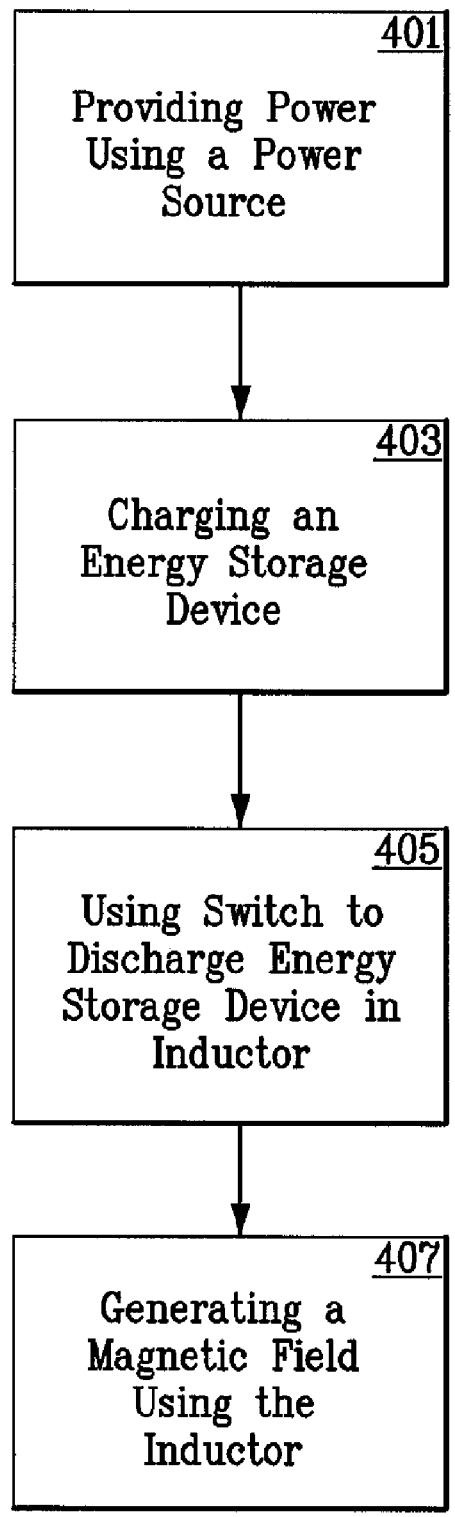
FIG. 4 is a flowchart illustrating an example method of producing a magnetic field in accordance with an embodiment.

An additional possible benefit of the use of IGBT 120 as a switching element, and the power savings that result therefrom, may be the reduction in size of a magnetic stimulation device to the point at which such a device may be designed to be highly portable. For example, such a device may be housed in a briefcase or other small container. Such a device may be adapted for use by a non-medical professional, such as the patient. FIG. 4 is a flowchart illustrating an example method 400 of producing a magnetic field in accordance with an embodiment. At 401, power is provided using a power source such as, for example, power supply 116 as discussed above in connection with FIGS. 1 and 2. At 403, an energy storage device or devices, such as capacitor 114 as discussed above in connection with FIGS. 1 and 2, is charged by the power source. It should be appreciated that in an alternative embodiment 403 need not be performed if, for example, the power source generates sufficient power that a charged capacitor is not needed for the intended application. At 405, a switch is used to discharge the energy storage device into an inductor. In an embodiment, the switch may be IGBT 120 as discussed above in connection with FIG. 2 and the inductor may be inductor 110 as discussed above in connection with FIGS. 1 and 2. In an alternative embodiment discussed above where a capacitor is not present, the switch may simply switch the power source on to provide power to the inductor. At 407, a magnetic field may be generated using the inductor. It will be appreciated that any or all of 401-407 may be repeated as many times as appropriate for the intended application.

It is to be understood that the foregoing illustrative embodiments have been provided merely for the purpose of explanation and are in no way to be construed as limiting of the invention. Words used herein are words of description and illustration, rather than words of limitation. In addition, the advantages and objectives described herein may not be realized by each and every embodiment practicing the present invention. Further, although the invention has been described herein with reference to particular structure, materials and/or embodiments, the invention is not intended to be limited to the particulars disclosed herein. Rather, the invention extends to all functionally equivalent structures, methods and uses, such as are within the scope of the appended claims.

For example, although the disclosure addresses the treatment of patients, it should be appreciated that techniques described herein also contemplate patient diagnosis. In fact, where the disclosure refers to the treatment of patients for certain conditions, the techniques equally apply to the monitoring and diagnosis of patients for the same or similar conditions.

Those skilled in the art, having the benefit of the teachings of this specification, may affect numerous modifications thereto and changes may be made without departing from the scope and spirit of the invention.

What is claimed is:

1. A magnetic stimulation device, comprising:
   an inductor for generating a magnetic field;
   a power source for providing power; and
   a semiconductor switching device that operatively couples the inductor and power source, wherein the semiconductor switching device directs power from the power source to the inductor to generate the magnetic field at a resonant frequency.

2. The device of claim 1, wherein the inductor is a ferromagnetic core stimulation coil.

3. The device of claim 1, wherein the inductor comprises a high saturation core material.

4. The device of claim 1, wherein the inductor is formed having a thin core TMS coil design.

5. The device of claim 1, wherein the inductor is formed having an air core.

6. The device of claim 5, wherein the inductor is substantially formed in any one of a figure eight shape, a circular shape, a conical shape and a double conical shape.

7. The device of claim 1, wherein the device is adapted to be substantially portable.

8. The device of claim 1, wherein the generated magnetic field is in the form of a magnetic pulse.

9. The device of claim 8, wherein the magnetic pulse has a pulse width of less than 200 µs is in duration.

10. The device of claim 8, wherein the magnetic pulse has a pulse width that is substantially 100 µs in duration.

11. The device of claim 8, wherein the magnetic pulse has at least one characteristic that is adapted to stimulate a cortical neuron.

12. The device of claim 1, wherein the power source comprises an AC power supply and a battery.

13. The device of claim 1, wherein the power source comprises a DC power supply.

14. The device of claim 1, wherein the power source comprises a battery.

15. The device of claim 1, wherein the semiconductor switching device is an Integrated Gate Commutated Thyristor (IGCT).

16. The device of claim 1, wherein the semiconductor switching device is an Insulated Gate Bipolar Transistor (IGBT).

17. The device of claim 16, further comprising a commutating diode connected to the IGBT in parallel for reducing a high voltage transient across the IGBT.

18. The device of claim 1, further comprising an energy storage device, wherein the power supply charges the energy storage device and the semiconductor switching device directs power from the power source to the inductor by causing the energy storage device to discharge into the inductor to generate the magnetic field.

19. The device of claim 18, wherein the energy storage device is at least one capacitor.

20. The device of claim 18, wherein the energy storage device is the power source.

21. The device of claim 18, wherein the energy storage device is a battery.

22. The device of claim 1, wherein the generated magnetic field is configured for one of: transcranial magnetic stimulation (TMS), repetitive transcranial magnetic stimulation (rTMS), magnetic seizure therapy (MST) and peripheral nerve stimulation.

23. A method, comprising:
   providing power using a power source;
   operatively coupling the power source to an inductor using a semiconductor switching device;
   directing power from the power source to the inductor using the semiconductor switching device; and
   generating the magnetic field at a resonant frequency using the inductor.

24. The method of claim 23, wherein the inductor is a ferromagnetic core stimulation coil.

25. The method of claim 23, wherein the inductor comprises a high saturation core material.

26. The method of claim 23, wherein the inductor is formed having a thin core TMS coil design.

27. The method of claim 23, wherein the inductor is formed having an air core.

28. The method of claim 27, wherein the inductor is substantially formed in any one of a figure eight shape, a circular shape, a conical shape and a double conical shape.

29. The method of claim 23, wherein said providing, operatively coupling, directing and generating are performed by a device that is adapted to be substantially portable.

30. The method of claim 23, wherein generating a magnetic field comprises generating a magnetic pulse.

31. The method of claim 23, wherein the magnetic pulse has a pulse width of less than 200 µs is in duration.

32. The method of claim 23, wherein the magnetic pulse has a pulse width that is substantially 100 µs in duration.

33. The method of claim 23, wherein the magnetic pulse has at least one characteristic that is adapted to stimulate a cortical neuron.

34. The method of claim 23, wherein the power source comprises an AC power supply and a battery.

35. The method of claim 23, wherein the power source comprises a DC power supply.

36. The method of claim 23, wherein the power source comprises a battery.

37. The method of claim 23, further comprising charging an energy storage device using the power supply, and wherein directing power from the power source to the inductor using the semiconductor switching device comprises causing the energy storage device to discharge into the inductor to generate the magnetic field.

38. The method of claim 37, wherein the energy storage device is at least one capacitor.

39. The method of claim 37, wherein the energy storage device is the power source.

40. The method of claim 37, wherein the energy storage device is a battery.

41. The method of claim 23, wherein the generated magnetic field is configured for one of: transcranial magnetic stimulation (TMS), repetitive transcranial magnetic stimulation (rTMS), magnetic seizure therapy (MST) and peripheral nerve stimulation.

42. The method of claim 23, wherein the semiconductor switching device is an Insulated Gate Bipolar Transistor (IGBT).

43. The method of claim 42, further comprising reducing a high voltage transient across the IGBT using a commutating diode that is connected to the IGBT in parallel.

44. The method of claim 23, wherein the semiconductor switching device is an Integrated Gate Commutated Thyristor (IGCT).

* * * * *

UNITED STATES PATENT AND TRADEMARK OFFICE
CERTIFICATE OF CORRECTION

PATENT NO. : 7,744,523 B2
APPLICATION NO. : 11/759537
DATED : June 29, 2010
INVENTOR(S) : Charles M. Epstein It is certified that error appears in the above-identified patent and that said Letters Patent is hereby corrected as shown below:

IN THE SPECIFICATION

At column 1, after "DRIVE CIRCUIT FOR MAGNETIC STIMULATION" and before "BACKGROUND", insert --GOVERNMENT RIGHTS OF APPLICATION--.

At column 1, after "GOVERNMENT RIGHTS OF APPLICATION", insert --This invention was made with Government support under the contract DAAD19-02-C-0048 awarded by Defense Advanced Research Projects Agency (DARPA). The Government has certain rights in the invention--.

Signed and Sealed this
Twentieth Day of October, 2015

Michelle K. Lee
*Director of the United States Patent and Trademark Office*